US009597255B2

(12) United States Patent
Oki et al.

(10) Patent No.: US 9,597,255 B2
(45) Date of Patent: Mar. 21, 2017

(54) GUM MASSAGING TOOL

(75) Inventors: Takehiko Oki, Otsu (JP); Tatsuhiko Oki, Otsu (JP); Narisato Kanamura, Kyoto (JP); Toshiro Yamamoto, Kyoto (JP); Ken-ichi Honjo, Kyoto (JP)

(73) Assignees: OHGI TECHNOLOGICAL CREATION CO., LTD., Shiga (JP); KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 478 days.

(21) Appl. No.: 13/808,960

(22) PCT Filed: Nov. 8, 2011

(86) PCT No.: PCT/JP2011/075756
§ 371 (c)(1),
(2), (4) Date: Jan. 8, 2013

(87) PCT Pub. No.: WO2012/063835
PCT Pub. Date: May 18, 2012

(65) Prior Publication Data

US 2013/0123675 A1 May 16, 2013

(30) Foreign Application Priority Data

Nov. 8, 2010 (JP) ................................ 2010-250239

(51) Int. Cl.
*A61F 7/00* (2006.01)
*A61H 13/00* (2006.01)
*A61H 23/02* (2006.01)

(52) U.S. Cl.
CPC ......... *A61H 13/00* (2013.01); *A61H 23/0254* (2013.01); *A61H 2201/0153* (2013.01);
(Continued)

(58) Field of Classification Search
CPC .......... A61H 1/00; A61H 1/005; A61H 13/00; A61H 23/00; A61H 23/02; A61H 23/0254;
(Continued)

(56) References Cited

U.S. PATENT DOCUMENTS 3,563,233 A * 2/1971 Bodine .......................... 601/72
4,219,619 A * 8/1980 Zarow .......................... 433/118
(Continued)

FOREIGN PATENT DOCUMENTS

JP 63-11176 A 1/1988
JP 5-95527 U 12/1993
(Continued)

OTHER PUBLICATIONS

Official Communication issued in International Patent Application No. PCT/JP2011/075756, mailed on Feb. 7, 2012.
(Continued)

*Primary Examiner* — Steven Douglas
(74) *Attorney, Agent, or Firm* — Keating & Bennett, LLP

(57) ABSTRACT

A gum massaging tool includes a handle portion which accommodates electric or mechanical members and in which a selector switch is provided in an exposed manner; a fixed shaft portion that is fixed to the handle portion so as to extend from one end of the handle portion and is heated according to an operation of the selector switch; a gum contact portion that is rotatable around a distal end portion of the fixed shaft portion and that includes a carbon body which receives heat from the fixed shaft portion and transfers the heat to a gum contacting surface; and a supporting portion that is rotatably engaged with and supports the gum contact portion and is detachably attached to the handle portion.

4 Claims, 6 Drawing Sheets

(52) U.S. Cl.
CPC ................ *A61H 2201/0207* (2013.01); *A61H 2201/0228* (2013.01); *A61H 2201/10* (2013.01); *A61H 2201/1692* (2013.01)

(58) Field of Classification Search
CPC ............ A61H 23/0263; A61H 2201/02; A61H 2201/0207; A61H 2201/0228; A61H 2201/12; A61H 2201/1207; A61H 2201/1215; A61H 2201/0153; A61H 2201/10; A61H 2201/1692
USPC . 601/112, 46, 139, 141, 142, 67, 69, 70, 72, 601/73, 136; 433/114, 141
See application file for complete search history.

(56) References Cited

U.S. PATENT DOCUMENTS

| | | | | |
|---|---|---|---|---|
| 4,299,208 | A * | 11/1981 | Blanc | 601/141 |
| 4,845,796 | A * | 7/1989 | Mosley | 15/23 |
| 5,718,667 | A * | 2/1998 | Sugimoto et al. | 601/139 |
| 6,183,427 | B1 * | 2/2001 | Ishii | 601/46 |
| 6,322,583 | B1 * | 11/2001 | Tu et al. | 607/96 |
| 7,832,954 | B2 * | 11/2010 | Gueret | 401/129 |
| 2007/0161931 | A1 | 7/2007 | Kunita et al. | |
| 2007/0265555 | A1 * | 11/2007 | Deng | 601/141 |
| 2012/0199553 | A1 | 8/2012 | Koga et al. | |

FOREIGN PATENT DOCUMENTS

| | | | |
|---|---|---|---|
| JP | 2002-119562 | A | 4/2002 |
| JP | 2002-153496 | A | 5/2002 |
| JP | 3147663 | U | 1/2009 |
| JP | 4280506 | B2 | 6/2009 |
| JP | 2009-189431 | A | 8/2009 |
| JP | 2009-195660 | A | 9/2009 |
| JP | 2010-030899 | A | 2/2010 |
| WO | 2006/068215 | A1 | 6/2006 |

OTHER PUBLICATIONS

Official Communication issued in corresponding Japanese Patent Application No. 2013-254291, mailed on Aug. 28, 2015.

English translation of Official Communication issued in corresponding Japanese Patent Application No. 2015-209887, mailed on Sep. 7, 2016.

* cited by examiner

GUM MASSAGING TOOL

BACKGROUND OF THE INVENTION

1. Field of the Invention

The present invention relates to a gum massaging tool for massaging gums.

2. Description of the Related Art

Conventionally, in order to maintain intraoral health, in addition to brushing with a toothbrush, a gum massage which is an operation of massaging gums to promote blood circulation is often done with the aim to prevent pyorrhea and gingivitis.

Although a gum massage may be easily done using a hard-bristle toothbrush, since the surface of gums may be damaged due to application of excessive force, a dedicated gum massaging tool that rarely damages the gums has been proposed. For example, a gum massaging tool disclosed in Japanese Utility Model Application Publication No. 05-095527 is configured to massage the gums by pressing a roller against the gums so as to reciprocate with appropriate force so that only the pressure of the roller acts on the gums. Moreover, a gum massaging tool disclosed in Japanese Patent Application Publication No. 2009-189431 is configured to include a soft gum contact portion in which a plurality of hemispheric protrusions is formed and a magnet at a distal end portion of a vibrating shaft so that only vibration and magnetic force act on the gums.

However, the conventional gum massaging tools including that disclosed in Japanese Utility Model Application Publication No. 5-95527 and Japanese Patent Application Publication No. 2009-189431 are considered to have room for improvement with respect to massaging effect, specifically, in the perspective of further promoting blood circulation to the gums.

SUMMARY OF THE INVENTION

Preferred embodiments of the present invention provide a gum massaging tool that can further promote blood circulation to the gums and which rarely damages surfaces of gums.

A gum massaging tool according to a preferred embodiment of the present invention includes a handle portion which accommodates electrical or mechanical members and in which a selector switch is provided in an exposed manner; a fixed shaft portion that is fixed to the handle portion so as to extend from one end of the handle portion; a gum contact portion that is disposed so as to be rotatable around a distal end portion of the fixed shaft portion and includes a carbon body; and a supporting portion that is rotatably engaged with and supports the gum contact portion and that is detachably attached to or is provided integrally with the handle portion.

Preferably, the fixed shaft portion is heated according to an operation on the selector switch, and the carbon body of the gum contact portion receives heat from the fixed shaft portion and transfers the heat to a surface that comes into contact with the gum.

Preferably, the fixed shaft portion is vibrated according to an operation on the selector switch.

Preferably, the gum contact portion includes a coating of diamond-like carbon which is provided on a surface of the carbon body.

Preferably, the carbon body has a non-penetrating insertion hole in which the fixed shaft portion is inserted.

Preferably, the gum contact portion includes a plurality of approximately hemispheric soft elastic protrusions which is arranged on a circumferential surface of the carbon body.

According to the gum massaging tool of a preferred embodiment of the present invention, it is possible to press the gum contact portion of which the temperature is increased against the gums and to massage the gums while effectively increasing the temperature of the gums with heat conduction and far-infrared radiation from the carbon body. As a result, it is possible to further promote blood circulation in the gums. Further, since only the pressure of the gum contact portion that rotates acts on the gums, the surfaces of the gums are rarely, if ever, damaged.

The above and other elements, features, steps, characteristics and advantages of the present invention will become more apparent from the following detailed description of the preferred embodiments with reference to the attached drawings.

BRIEF DESCRIPTION OF THE DRAWINGS

FIGS. 1A and 1B show a cross-section of a gum massaging tool 1 according to a preferred embodiment of the present invention, in which FIG. 1A is a schematic cross-sectional view and FIG. 1B is a cross-sectional view showing the vicinity of a fixed shaft portion 3 at an enlarged scale.

FIGS. 2A and 2B show an appearance of the gum massaging tool 1 according to a preferred embodiment of the present invention at a reduced scale, in which FIG. 2A is a perspective view and FIG. 2B is a perspective view when observed from a bottom surface side.

FIGS. 5A and 5B show a modification of a preferred embodiment of a gum contact portion 4 of the gum massaging tool according to the present invention at an enlarged scale, in which FIG. 5A is a front view and FIG. 5B is a cross-sectional view.

DETAILED DESCRIPTION OF THE PREFERRED EMBODIMENTS

Figure 1A:
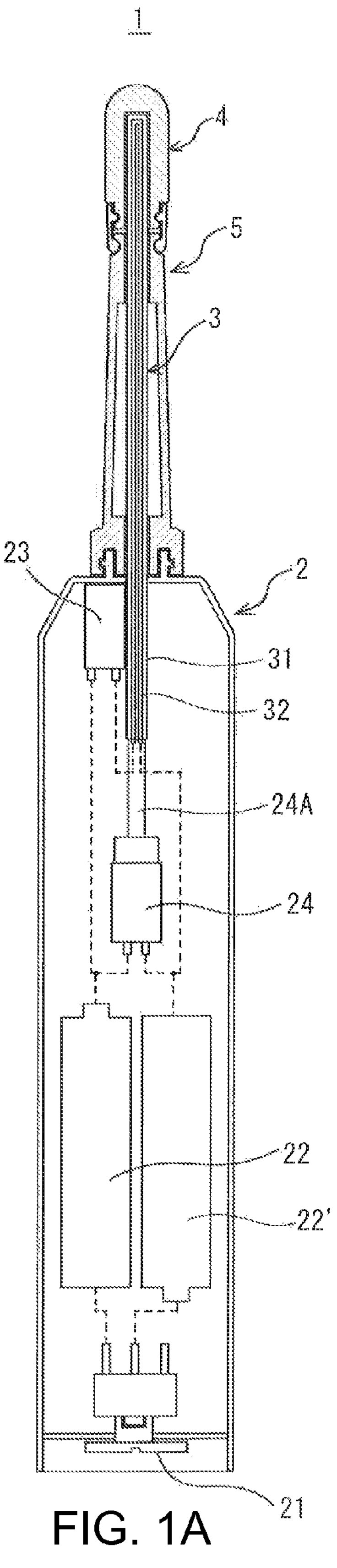

Hereinafter, preferred embodiments of the present invention will be described with reference to the drawings. As shown in FIGS. 1A and 1B and FIGS. 2A and 2B, a gum massaging tool 1 according to a preferred embodiment of the present invention preferably includes an elongated handle portion 2, a fixed shaft portion 3 that is fixed to the handle portion 2 so as to extend from one end of the handle portion 2, a gum contact portion 4 that is disposed so as to be rotatable around a distal end portion of the fixed shaft portion 3, and a supporting portion 5 that is rotatably engaged with and supports the gum contact portion 4 and is detachably attached to the handle portion 2. In FIG. 1A, electric or mechanical members and electric wires thereof (depicted by broken lines) are schematically shown as an inner configuration of the handle portion 2.

The handle portion 2 is preferably a long (that is, approximately tube-like) case, and a selector switch 21 is preferably provided at a bottom portion of the handle portion 2 in an exposed manner so that the selector switch 21 can be operated from the outside. Further, the handle portion 2 preferably accommodates batteries 22 and 22', a thermostat 23, a motor 24, and the like which are electric or mechanical members. According to an operation on the selector switch 21, the batteries 22 and 22' supply power to a heating element 32 (described later) to heat the heating element 32 in order to heat the fixed shaft portion 3 and supply power to the motor 24 to cause the motor 24 to perform a rotational movement in order to vibrate the fixed shaft portion 3. The rotational movement of the motor 24 generates vibration, and the vibration is preferably transmitted to the fixed shaft portion 3 through a vibration transmission device 24A.

In this preferred embodiment shown in FIG. 1A, two states of ON and OFF can be selected by the selector switch 21, and in the ON state, the fixed shaft portion 3 is heated and vibrated. More specifically, electric wires are arranged between a positive terminal of the battery 22 and one terminal of the thermostat 23, between the other terminal of the thermostat 23 and one terminal of the heating element 32, and between the other terminal of the heating element 32 and a negative terminal of the battery 22'. Further, electric wires are arranged between the positive terminal of the battery 22 and one terminal of the motor 24 and between the other terminal of the motor 24 and the negative terminal of the battery 22'. Furthermore, electric wires are arranged between the positive terminal of the battery 22' and one terminal of the selector switch 21 and between the other terminal of the selector switch and the negative terminal of the battery 22. In the OFF state (a state where the selector switch 21 is slid to the right in the figure), the two batteries 22 and 22' are not electrically connected. In the ON state (a state where the selector switch 21 is slid to the left in the figure), the two batteries 22 and 22' are electrically connected such that the heating element 32 and the motor 24 are in the conduction state, and the fixed shaft portion 3 is heated and vibrated.

The selector switch 21, the electric or mechanical members, and the electric wires thereof can be appropriately changed in any desirable manner according to specifications. For example, two selector switches 21 may be arranged so that the fixed shaft portion 3 is heated and vibrated independently in the ON state of each switch. Further, the block of the batteries 22 and 22' may be replaced with one or three or more primary batteries and rechargeable batteries, for example, and the batteries 22 and 22' may be charged in a mounted state.

The thermostat 23 is configured and programmed to control the temperature of the surface of the gum contact portion 4 such that a portion of the gum contact portion 4 that makes contact with the gums to be maintained at an appropriate temperature (for example, highest temperature of approximately 40° C. to approximately 45° C.). A temperature detecting portion of the thermostat 23 is preferably arranged to be in contact with a fixed shaft body 31 (described later). The thermostat 23 controls conduction of the heating element 32 according to the temperature detected by the temperature detecting portion.

The fixed shaft portion 3 includes the fixed shaft body 31 (made from, for example, aluminum, stainless steel, etc.) that has high heat conductivity and a bottomed cylindrical shape and the heating element 32 that is provided inside the fixed shaft body 31 so as to generate heat according to electricity conduction. For example, a member in which a nichrome wire coated with an insulator is arranged so as to reciprocate from the vicinity of a base end of the fixed shaft body 31 to the vicinity of the distal end of the fixed shaft body 31 may be used as the heating element 32. The fixed shaft body 31 is heated by the heating element 32 and transfers the heat to the gum contact portion 4, and the temperature of the gum contact portion 4 is detected by the thermostat 23.

When a user presses the gum massaging tool 1 against the gums and causes the gum massaging tool 1 to perform a reciprocating movement, the gum contact portion 4 rotates following the reciprocating movement. The gum contact portion 4 preferably includes, as its main member, a carbon body 41 that receives heat from the fixed shaft portion 3 and transfers the heat to a surface that comes into contact with the gums and further includes, as its accessory member, a connecting member arranged to connect the gum contact portion 4 to the supporting portion 5.

The carbon body 41 is preferably a body in which carbon crystal structures that are, for example, condensed by baking are generally integrated with each other. The crystal structures can preferably be made approximately isotropic so that the directions of the structures are not generally biased. The carbon body 41 can be produced in the following manner. That is, roughly 5 wt % of binders are added to carbon powder of graphite or carbide (e.g., bamboo coal) and are hardened, and hydraulic pressure or the like is isotropically applied to obtain a lump of a predetermined shape (for example, a rectangular or substantially rectangular shape). The obtained lump is preferably heated in an oxygen deficient state and is baked over a long period at approximately 2500° C. to approximately 3500° C. In this state, carbon powders in the raw material bond with each other and carbons are crystallized (i.e., graphitized). The binders are volatilized at roughly 1000° C. to roughly 1200° C. in the course of heating. After that, heating is stopped to decrease the temperature, and the lump is processed to a desired shape. Since the binders are volatilized, carbon constitutes approximately 100% (for example, 99% or more) of the carbon body obtained in this manner. Further, a bulk density (bulk specific weight) is preferably approximately 1.77 $Mg/m^3$ or more, for example.

Figure 3:
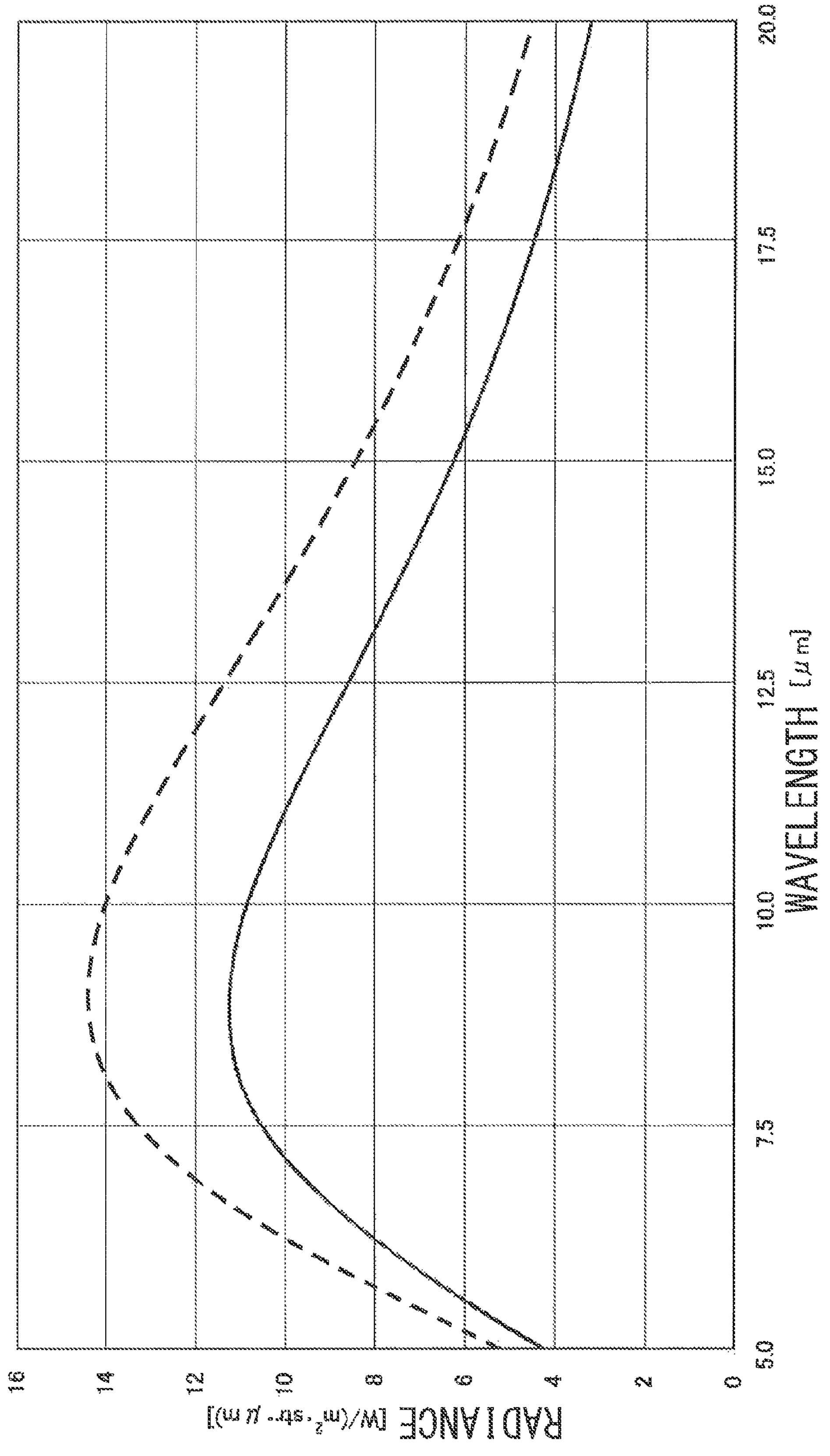
FIG. 3 is a characteristic diagram depicting far-infrared radiation of a carbon body according to a preferred embodiment of the present invention.

Since the entire carbon body 41 is combined by the crystal structures, the carbon body 41 has high physical strength and high heat conductivity (approximately 100 W/(m·K) to approximately 140 W/(m·K)). Further, the carbon body 41 radiates a large amount of far-infrared rays (see FIG. 3), which increases as the temperature increases. FIG. 3 shows far-infrared radiation characteristics of a carbon body having dimensions of 25×25×2 (mm), produced in the same manner as the method of producing the carbon body 41 in accordance with the above described preferred embodiment of the present invention. A solid line shows radiance of a carbon body and a broken line shows radiance of a black body. A Fourier transform infrared spectrophotometer (in this case, a JIR-5500 type equipped with an infrared radiation unit IR-IRR200 manufactured by JEOL Ltd.) was used as an analysis device, and the measurement temperature was 50° C.

Figure 1B:
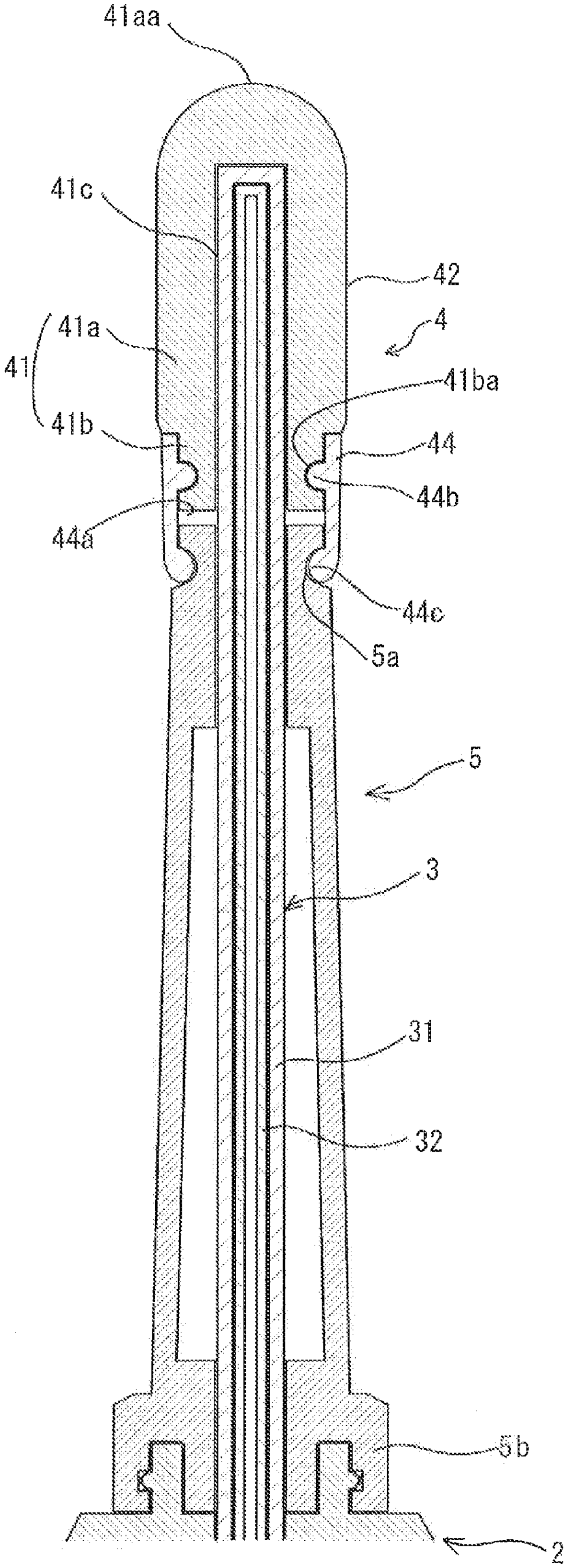
Figure 2B:
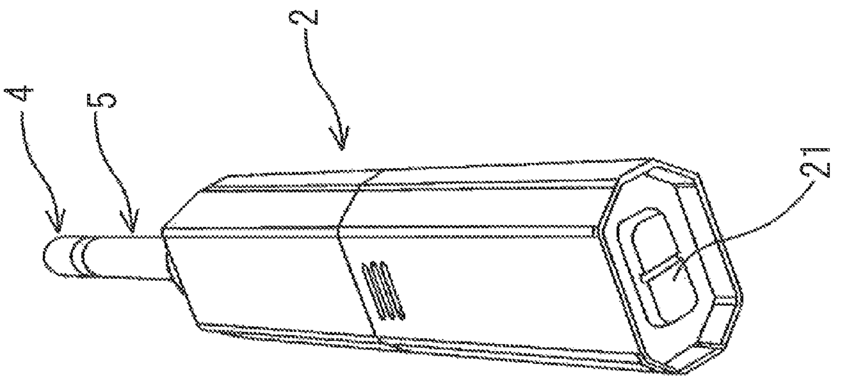
Figure 2A:
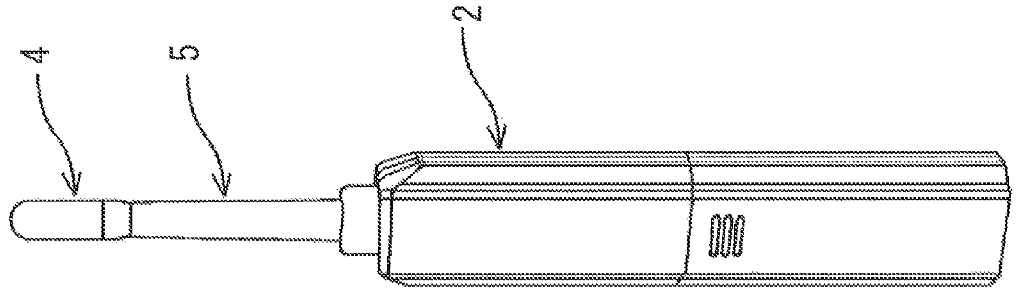

As shown in FIG. 1B, the carbon body 41 preferably has a cylindrical or substantially cylindrical shape and has a configuration in which a large-diameter body portion 41*a* that makes contact with the gums and a small-diameter attachment portion 41*b* are integrally provided together in an axial direction as a single monolithic member. An insertion hole 41*c* in which the fixed shaft portion 3 is inserted is arranged at the position of a central axis of these portions 41*a* and 41*b*.

Figure 4:
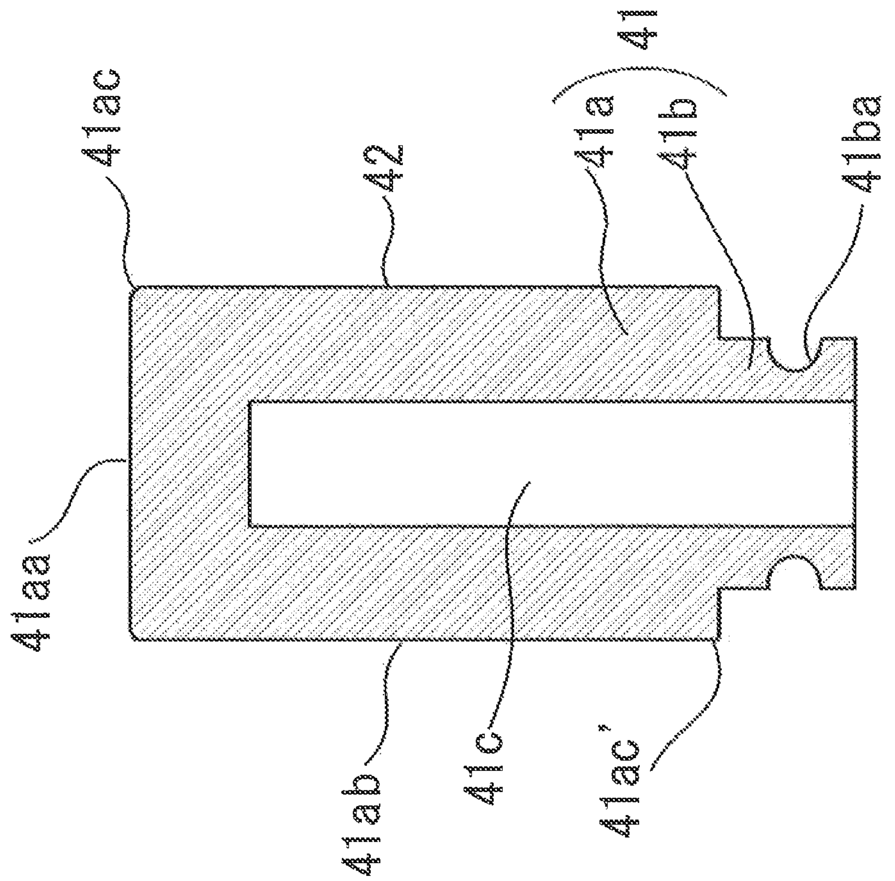
FIG. 4 is an enlarged cross-sectional view showing a modification of a preferred embodiment of a carbon body 41 of the gum massaging tool 1 according to the present invention.

The body portion 41*a* can be defined, for example, such that an outer diameter is approximately 8 mm to approximately 10 mm and a length in the axial direction is approximately 15 mm to approximately 25 mm, and the inner diameter of the insertion hole 41*c* may be set to approximately 3 mm. Further, the body portion 41*a* may have various shapes so that the body portion 41*a* can easily make contact with the gums. For example, the body portion 41*a* shown in FIG. 1B preferably includes a rounded distal end portion 41*aa* with an approximately hemispheric shape. Alternatively, in accordance with another preferred embodiment of the present invention, corner portions 41*ac* and 41*ac*' with a small R-portion may preferably be provided at both ends of an outer side surface portion 41*ab* as shown in FIG. 4.

The attachment portion 41*b* preferably includes a ring-shaped groove portion 41*ba* that is provided on an outer circumferential surface so that the connecting member 44 is fitted to the attachment portion 41*b*.

The inner diameter of the insertion hole 41*c* preferably is set to be slightly larger (for example, by approximately 0.1 mm) than the outer diameter of the fixed shaft portion 3 so that heat conduction from the fixed shaft portion 3 to the carbon body 41 is not disturbed as much as possible, and so that the rotation of the gum contact portion 4 is not disturbed as much as possible so that the fixed shaft portion 3 and the carbon body 41 do not make contact with each other. Further, the insertion hole 41*c* preferably does not penetrate to the distal end portion 41*aa* of the body portion 41*a*. By doing so, preferably no foreign material can enter into the insertion hole 41*c* from the distal end portion 41*aa*, and the distal end portion 41*aa* can be effectively used for massaging.

A coating 42 (for example, having a thickness of approximately 2 μm to approximately 4 μm) of diamond-like carbon (DLC) is preferably provided on the surface of the carbon body of the gum contact portion 4. This diamond-like carbon coating 42 is preferably one in which carbon is vapor-grown according to plasma CVD, PVD, or the like to form crystalline carbon, and which has good adhesion to the carbon body 41 and is hard. Further, fluorine and/or silver, for example, may be mixed during vapor-phase growth of diamond-like carbon in order to obtain bactericidal properties.

Figure 5B:
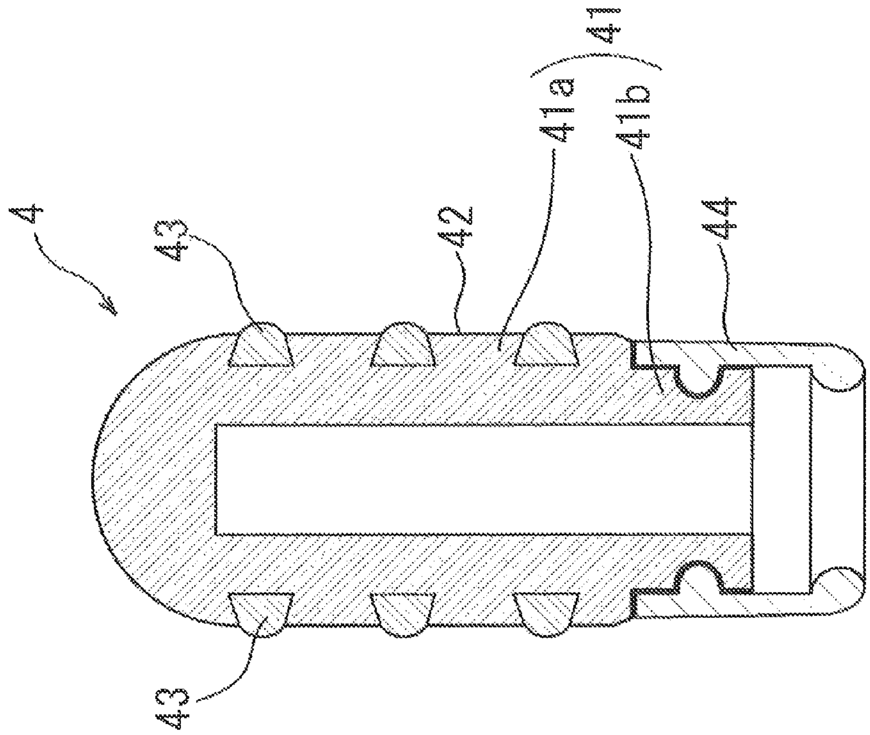
Figure 5A:
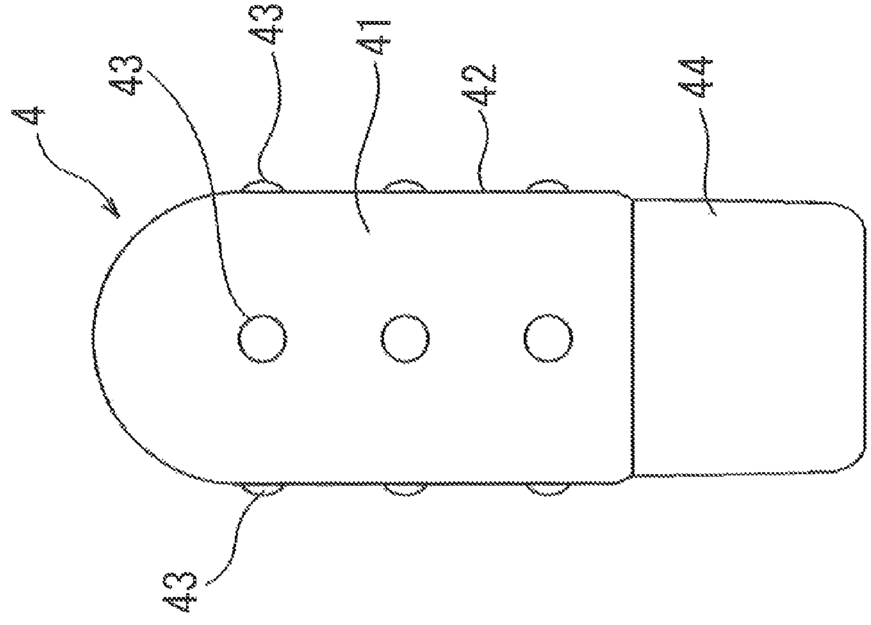

Further, as in a preferred embodiment of the present invention shown in FIGS. 5A and 5B, a plurality of approximately hemispheric soft elastic protrusions 43 may be provided on a circumferential surface of the carbon body 41 (the body portion 41*a*) of the gum contact portion 4. The elastic protrusions 43 preferably protrude a small distance (for example, approximately 0.2 mm to approximately 0.4 mm) from the surface of the carbon body 41. By doing so, it is possible to soften a sudden impact when the gum contact portion 4 comes into contact with the gums. The elastic protrusion 43 can be made from, for example, silicone rubber which is widely used in human body care. In order to make the elastic protrusions 43 difficult to be separated from the carbon body 1, it is preferable to provide the elastic protrusions 43 within holes of the carbon body 41 that are approximately trapezoidal in cross-section by filling a liquid material (e.g., silicone rubber) into the holes, and hardening the material to have approximately hemispheric surfaces on the holes.

The connecting member 44 is preferably an approximately barrel-shaped member that connects the carbon body and the supporting portion 5. The connecting member 44 includes a hollow portion 44*a* that is open so that the attachment portion 41*b* of the carbon body 41 is inserted from one end thereof and the supporting portion 5 is inserted from the other end thereof. A first ring-shaped protruding portion 44*b* that is fitted to the groove portion 41*ba* of the attachment portion 41*b* is preferably defined on an inner side surface of the hollow portion 44*a*. Further, a second ring-shaped protruding portion 44*c* is preferably further defined on the inner side surface of the hollow portion 44*a*.

The supporting portion 5 preferably is an elongated member, and a penetration hole in which the fixed shaft portion 3 is inserted is provided along the central axis. A ring-shaped groove portion 5*a* is preferably defined at one end portion of the supporting portion 5, and the supporting portion 5 is rotatably engaged with the connecting member 44 of the gum contact portion 4 (that is, the supporting portion 5 is connected to the connecting member 44 in a rotatable state). Further, a docking mechanism 5*b* that allows the supporting portion 5 to be detachably attached to the handle portion 2 is preferably provided at the other end of the supporting portion 5.

Figure 6:
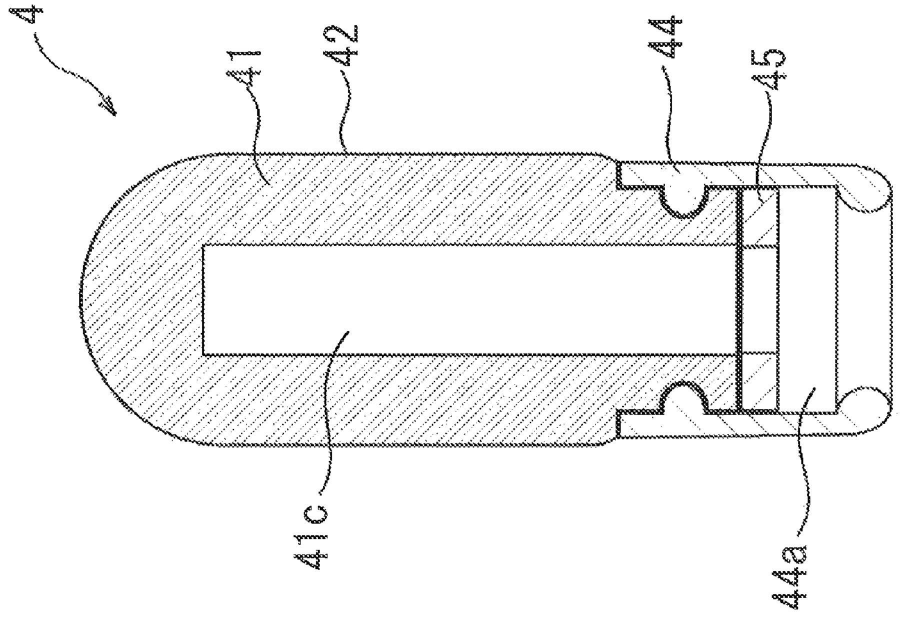
FIG. 6 is a cross-sectional view showing another modification of the gum contact portion 4 of the gum massaging tool 1 at an enlarged scale.

As described above, the gum massaging tool 1 has a configuration in which the gum contact portion 4 is rotatably engaged with and supported by the supporting portion 5, and the fixed shaft portion 3 is inserted into the gum contact portion 4 and the supporting portion 5 along the central axis of the gum contact portion 4 and the supporting portion 5. The fixed shaft portion 3 is fixed to the handle portion 2, and the supporting portion 5 in the use state is fixed to the handle portion 2. With such a configuration, the outer diameter of the gum contact portion 4 can be decreased sufficiently so that the gum contact portion 4 reaches the inner portions of the gums. Further, as in a preferred embodiment of the present invention shown in FIG. 6, a bearing 45 may be provided in the gum contact portion 4, and the inner diameter of the bearing 45 may be set to be smaller than the inner diameter of the insertion hole 41*c* of the carbon body 41 so that a gap is easily secured between the inner side surface of the insertion hole 41*c* and the fixed shaft portion 3. In FIG. 6, the bearing 45 is provided in the hollow portion 44*a* of the connecting member 44 of the gum contact portion 4.

A method of using the gum massaging tool 1 is as follows. That is, the user operates the selector switch 21 by holding the handle portion 2 with a hand to heat and vibrate the fixed shaft portion 3, places the gum contact portion 4 inside the mouth, and massages the gums by pressing the gum massaging tool 1 against the gums and causing the gum massaging tool 1 to perform a reciprocating movement with an appropriate force.

The gum contact portion 4 rotates following the reciprocating movement. That is, sliding (frictional motion) is rarely performed on the gums, but since only the pressure of the rotation of the gum contact portion 4 acts on the gums, the surface of the gums is rarely, if ever, damaged. Further, since the carbon body 41 has high physical strength and the coating 42 is hard, the gum contact portion 4 is rarely worn or damaged. Furthermore, since the constituent materials of the carbon body 41 and the coating 42 are preferably the same as those of the organic substance that constitutes the human body, the gums get accustomed to these members when these members come into contact with the gums, and thus, these members are highly safe for a human body. Since these members are not metal or plastics, naturally, these members do not cause metal allergies and chemical allergies.

When the fixed shaft portion 3 is heated according to the operation on the selector switch 21, the heat of the fixed shaft portion 3 is transferred to the carbon body 41 of the gum contact portion 4, and the temperature of the carbon body 41 increases. The carbon body 41 transfers heat directly to the gums according to heat conduction and radiates a larger amount of far-infrared rays as the temperature increases. The far-infrared radiation heats the deep portion of the gums. Since the temperature of the gums can be effectively increased by the conduction heat and the radiation heat of far-infrared rays, it is possible to further promote the blood circulation to the gums according to the synergy effect with the pressure of the gum contact portion 4.

Further, since the carbon body 41 has high heat conductivity, a decrease in the temperature between the insertion hole 41*c* in which the fixed shaft portion 3 is inserted and the surface portion is small. Thus, it is not necessary to overheat the heating element 32, and the thermostat 23 that is in contact with the fixed shaft body 31 can perform temperature control with satisfactory accuracy.

Furthermore, when the fixed shaft portion 3 is vibrated according to the operation on the selector switch 21, the vibration is transmitted to the gums via the gum contact portion 4. This vibration can further promote the blood circulation to the gums.

An experiment to heat (up to about 37° C. and about 42° C.) gingival fibroblast and an experiment to apply vibration to gingival fibroblast were conducted using the gum massaging tool 1. The experiment results showed that the fibroblast growth factor (FGF-2) was increased approximately 2.5 times to approximately 3.5 times and the nerve growth factor (NGF) was increased approximately 1.2 times to approximately 1.3 times. The FGF-2 and the NGF respectively have the effect of growing fibroblast and the effect of promoting cell repair.

While the gum massaging tool 1 according to preferred embodiments of the present invention has been described, the present invention is not limited to that which is described in the preferred embodiments, and various changes can be made without departing from the scope of the present invention. For example, in some cases, a heating function may be not provided to the gum massaging tool 1. In this case, the carbon body 41 may be pressed against the gums after heat is transferred from the outside to the carbon body 41. Further, in some cases, a vibrating function may be not provided to the gum massaging tool 1. In this case, the motor 24 and the like are not necessary.

Further, the connecting member 44 of the gum contact portion 4 may be provided integrally with the supporting portion 5, and the first protruding portion 44*b* of the connecting member 44 may be rotatably engaged with the groove portion 41*ba* of the carbon body 41 so that the gum contact portion 4 can be rotated in relation to the supporting portion 5. Thus, in this case, the connecting member 44 is not included in the gum contact portion 4 but becomes a portion of the supporting portion 5. Further, in some cases, the supporting portion 5 may be provided integrally with the handle portion 2 so that the supporting portion 5 is not detachable from the handle portion 2.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A gum massaging tool comprising:

a handle portion which accommodates electrical or mechanical members and in which a selector switch is provided in an exposed manner;

a heating element that is heated by supplied power in response to an operation on the selector switch;

a gum contact portion that includes only one carbon body in which carbon crystal structures are condensed by baking and integrated with each other, the carbon body transfers heat from the heating element directly to gums by heat conduction and radiates an increasing amount of far-infrared rays with increasing temperature, so that the temperature of the gums is increased by a conduction heat and a radiation heat of the far-infrared rays;

a temperature detecting portion that detects a temperature so as to control the heating element; and a supporting portion that is an elongated member and supports the gum contact portion and that is connected to the handle portion.

2. The gum massaging tool according to claim 1, wherein:

the electrical or mechanical members include a motor; and the gum contact portion is vibrated by a rotational movement of the motor by the supplied power in response to an operation of the selector switch.

3. The gum massaging tool according to claim 1, wherein the gum contact portion includes a coating of diamond-like carbon (DLC) which is located on a surface of the carbon body.

4. The gum massaging tool according to claim 1, wherein the gum massaging tool maintains a temperature of the gums at about 37° C.

* * * * *